US008293813B2

(12) United States Patent
Troxel et al.

(10) Patent No.: US 8,293,813 B2
(45) Date of Patent: Oct. 23, 2012

(54) COHESIVE AND COMPRESSION RESISTANT DEMINERALIZED BONE CARRIER MATRIX

(75) Inventors: Karen Troxel, Warsaw, IN (US); Barbara Gibbs, West Lafayette, IN (US)

(73) Assignee: Biomet Manufacturing Corporation, Warsaw, IN (US)

( * ) Notice: Subject to any disclaimer, the term of this patent is extended or adjusted under 35 U.S.C. 154(b) by 85 days.

(21) Appl. No.: 12/397,959

(22) Filed: Mar. 4, 2009

(65) Prior Publication Data

US 2009/0227704 A1 Sep. 10, 2009

(51) Int. Cl.
*A61F 2/00* (2006.01)
*A61F 2/28* (2006.01)
*A61K 6/083* (2006.01)

(52) U.S. Cl. ..................... 523/115; 623/23.58
(58) Field of Classification Search .................. 523/115; 623/23.58
See application file for complete search history.

(56) References Cited

U.S. PATENT DOCUMENTS

| | | | |
|---|---|---|---|
| 4,294,753 A | 10/1981 | Urist | |
| 4,619,989 A | 10/1986 | Urist | |
| 4,976,736 A | 12/1990 | White | |
| 5,162,430 A | 11/1992 | Rhee et al. | |
| 5,264,214 A | 11/1993 | Rhee et al. | |
| 5,292,802 A | 3/1994 | Rhee et al. | |
| 5,304,595 A | 4/1994 | Rhee et al. | |
| 5,306,500 A | 4/1994 | Rhee et al. | |
| 5,308,889 A | 5/1994 | Rhee et al. | |
| 5,324,775 A | 6/1994 | Rhee et al. | |
| 5,328,955 A | 7/1994 | Rhee et al. | |
| 5,376,375 A | 12/1994 | Rhee et al. | |
| 5,470,911 A | 11/1995 | Rhee et al. | |
| 5,475,052 A | 12/1995 | Rhee et al. | |
| 5,510,121 A | 4/1996 | Rhee et al. | |
| 5,510,396 A * | 4/1996 | Prewett et al. | 523/113 |
| 5,510,418 A | 4/1996 | Rhee et al. | |
| 5,516,532 A * | 5/1996 | Atala et al. | 424/548 |
| 5,523,348 A | 6/1996 | Rhee et al. | |
| 5,543,441 A | 8/1996 | Rhee et al. | |
| 5,550,187 A * | 8/1996 | Rhee et al. | 525/54.1 |
| 5,565,519 A | 10/1996 | Rhee et al. | |
| 5,679,723 A * | 10/1997 | Cooper et al. | 523/115 |
| 5,700,289 A * | 12/1997 | Breitbart et al. | 424/423 |
| 5,874,500 A * | 2/1999 | Rhee et al. | 525/54.1 |
| 6,123,731 A * | 9/2000 | Boyce et al. | 623/23.63 |
| 6,311,690 B1 * | 11/2001 | Jefferies | 128/898 |
| 6,624,245 B2 * | 9/2003 | Wallace et al. | 525/54.1 |
| 6,911,212 B2 * | 6/2005 | Gertzman et al. | 424/426 |
| 7,045,141 B2 * | 5/2006 | Merboth et al. | 424/423 |
| 7,393,493 B2 * | 7/2008 | Ashman et al. | 264/496 |
| 7,838,022 B2 * | 11/2010 | Drapeau et al. | 424/423 |
| 2003/0143258 A1 * | 7/2003 | Knaack et al. | 424/426 |
| 2004/0002558 A1 * | 1/2004 | McKay | 523/115 |
| 2004/0019132 A1 * | 1/2004 | Long et al. | 523/115 |
| 2004/0243242 A1 * | 12/2004 | Sybert et al. | 623/17.16 |
| 2005/0020506 A1 * | 1/2005 | Drapeau et al. | 514/21 |
| 2005/0089578 A1 * | 4/2005 | Werkmeister et al. | 424/489 |
| 2005/0118230 A1 * | 6/2005 | Hill et al. | 424/426 |
| 2005/0147643 A1 * | 7/2005 | Hunter et al. | 424/423 |
| 2005/0203635 A1 * | 9/2005 | Hunter et al. | 623/23.72 |
| 2006/0083729 A1 * | 4/2006 | Kusanagi et al. | 424/94.1 |
| 2006/0199876 A1 * | 9/2006 | Troczynski et al. | 523/115 |
| 2006/0222680 A1 * | 10/2006 | Yang et al. | 424/426 |
| 2006/0251628 A1 * | 11/2006 | Attawia et al. | 424/93.7 |
| 2007/0190101 A1 * | 8/2007 | Yang et al. | 424/423 |
| 2007/0191963 A1 * | 8/2007 | Winterbottom et al. | 623/23.5 |
| 2008/0233203 A1 * | 9/2008 | Woodell-May et al. | 424/549 |
| 2008/0318862 A1 * | 12/2008 | Ashman et al. | 514/12 |
| 2010/0292146 A1 * | 11/2010 | Seibl et al. | 514/8.8 |

OTHER PUBLICATIONS

Hillig et al., J. Mater. Sci: Mater Med, 2008, 19:11-17.*
W.E. Hennick, C.F. Van Nostrum, "Novel crosslinking methods to design hydrogels," Advanced Drug Delivery Reviews, 54 (2002) 13-36.
Francesco M. Veronese, "Peptide and protein PEGylation: a review of problems and solutions," Biomaterials, 22 (2001) 405-417.
Francesco M. Veronese and Gianfranco Pasut, "PEGylation, successful approach to drug delivery," Drug Discovery Today, vol. 10, No. 21, Nov. 2005.
Pro Osteon 200R, Orthopedic Product Guide, 2012 Biomet Inc., www.orthopedicproductguide.com/bguide/User/Product/brief/2106/Pro-Osteon-200R.
Gorham et al, Effect of Chemical Modifications on the Susceptibility of Collagen to Proteoloysis.II. Dehydrothermal Crosslinking, Int.J. Biol.Macromol.,1992,129-138,14-3 Abstr.
Griebenow and Klibanov, Lyophilization-induced reversible changes in the secondary structure of proteins, Proc. Natl. Acad. Sci. USA, 1995, 10969-10976, v92.
Koide et al, A new type of biomaterial for artificial skin: Dehydrothermally cross-linked composites, J. Biomed. Materials. Research, 1993, 79-87, v27.
Lee et al, The effects of cross-linking of collagen-glycosaminoglycan scaffolds on compressive stiffness, chondrocyte-mediated contraction, proliferation and biosynthesis, Biomaterials, 2001, 3145-3154, v22-23, Abstract.
Miller, Collagen Amino Acid Composition, Extracellular Matrix Biochemistry. Piez & Reddi Eds., 1984, 64-67 (Ch.2), Elsevier Science Publishing, New York USA.
Stubbs et al, In vivo evaluation of resorbable bone graft substitutes in a rabbit tibial defect model, Biomaterials, 2004, 5037-5044, v.25.
Thompson & Czernuszka, The effect of two types of cross-linking on some mechanical properties of collagen, Biomed. Mater. Eng. 1995, 37-48, v.5-1 Abstract.
Wang et al, Collagen fibres with improved strength for the repair of soft tissue injuries, Biomaterials, 1994, 507-512, v.15-7.
Wang, Lyophilization and development of solid protein pharmaceuticals, Intl J Pharmaceutics, 2000, 1-60, v. 203.
Walsh et al, A resorbable porous ceramic composite bone graft substitute in a rabbit metaphyseal defect model, J. Orthopaedic Res., 2003, 655-661, v. 21.
Weadock et al, Physical crosslinking of collagen fibers: comparison of ultraviolet irradiation and dehydrothermal treatment, J. Biomed. Mater Res., 1995, 1373-9, v.29-11, Abst.
Weadock et al, Effect of physical crosslinking methods on collagen-fiber durability in proteolytic solutions, J. Biomed. Mater Res. 1996, 221-6, v.32-2, Abstract.

* cited by examiner

*Primary Examiner* — Liam Heincer
(74) *Attorney, Agent, or Firm* — Ryan O. White; Taft, Stettinius & Hollister, LLP

(57) ABSTRACT

The present invention provides a demineralized bone carrier matrix which is tolerant of bending, stretching and compression. The material comprises a carrier base material cross-linked with a multifunctional polymer. Demineralized bone matrix may be dispersed with the carrier matrix. The demineralized bone carrier matrix may be used as a bone graph substitute. Methods for making the carrier matrix are also provided.

8 Claims, No Drawings

COHESIVE AND COMPRESSION RESISTANT DEMINERALIZED BONE CARRIER MATRIX

BACKGROUND OF THE INVENTION

The present invention relates generally to carrier matrices for demineralized bone matrix and more particularly, to polyethylene oxide carrier matrices for demineralized bone matrix.

Demineralized bone matrix (DBM) is an effective substitute for autologous bone graft because it is both osteoinductive and osteoconductive. However, in the dry powder form, demineralized bone matrix powder is not easy to handle during surgery. For this reason, many different formulations and forms of demineralized bone matrix have been developed for the purpose of improving handling during surgery. Most of these formulations combine the DBM with a carrier that serves to bind the DBM particles together to form a paste or putty. Typical carriers are glycerol, polysaccharide solutions such as hyaluronic acid, lecithin, and gelatin. One problem with these puffy and paste formulations is that they remain malleable after implantation, and thereby can deform if subjected to compressive forces. One particular procedure in which bone grafts are subjected to compressive forces is postero-lateral spine fusions.

Another DBM-containing formulation having the property of macroscopic cohesiveness, as described above, can be produced by embedding DBM in a carrier matrix which is then be crosslinked with covalent intermolecular bonds. Such a crosslinked carrier would resist the drawbacks of uncrosslinked carriers, namely dissolving and deforming in vivo. However, most common crosslinking methods cannot be used without inactivating the bioactivity of the DBM. For instance, most chemical crosslinking agents, such as formaldehyde, glutaraldehyde, carbodiimides (e.g. 1-Ethyl-3-[3-dimethylaminopropyl]-carbodiimide hydrochloride) may crosslink protein carrier-matrices such as gelatin and collagen, but these chemical agents also interact with and deactivate the bioactive factors contained in the DBM such as bone morphogenic proteins. Another standard crosslinking technology, dehydrothermal crosslinking, is carried out at temperatures of 100° C. to 200° C., well above the temperature at which most proteins are denatured, including the bioactive components within the DBM.

As can be seen, there is a need for a carrier/matrix for active (osteoinductive) DBM which has macroscopic cohesiveness such that it does not dissolve, fall apart, or significantly deform in aqueous solutions or under mild compressive forces.

SUMMARY OF THE INVENTION

The present invention provides demineralized bone carrier matrix comprising a crosslinked matrix where the crosslinked matrix comprises a carrier base material crosslinked with a multifunctional polymer and demineralized bone matrix, wherein the demineralized bone is dispersed within the crosslinked matrix. The carrier base material may be collagen, gelatin formed from demineralized bone matrix (DBM), other proteins or protein rich samples such as polylysine, plasma, platelet rich plasma or protein poor plasma. Other polymers with substituents that allow crosslinking with the multifunctional polymer may be used. The multifunctional polymer may be any polymer with at least two functional groups.

The present invention also provides an osteoinductive demineralized bone carrier matrix comprising a crosslinked matrix, where the crosslinked matrix comprises a carrier base material crosslinked with a multifunctional poly(ethylene glycol), wherein the carrier base material is either a gelatin or collagen and wherein the multifunctional poly(ethylene glycol) has a functionality of about 2 to about 4 and demineralized bone matrix, wherein the demineralized bone matrix is dispersed throughout the crosslinked matrix.

The present invention further provides a bone graft substitute comprising a crosslinked matrix comprising a collagen or gelatin crosslinked with a multifunctional poly(ethylene glycol) and demineralized bone matrix wherein the demineralized bone is dispersed within the crosslinked matrix.

The present invention also provides a method of making a bone graft substitute comprising mixing a carrier base material solution with a multifunctional polymer solution to form a carrier matrix precursor, adding demineralized bone matrix to the carrier base material or the carrier matrix precursor, shaping the carrier matrix precursor; and gelling the carrier matrix precursor to form the bone graft substitute, wherein the bone graft substitute has the demineralized bone matrix disposed within.

These and other features, aspects and advantages of the present invention will become better understood with reference to the following description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides a demineralized bone carrier matrix which is osteoinductive, flexible and compression resistant. The demineralized bone carrier matrix may comprise a cross-linked matrix with DBM dispersed within, and possibly throughout, the cross-linked matrix. The DBM is able to retain osteoinductive activity within the cross-linked matrix. The carrier matrix may comprise a carrier base material and a multifunctional polymer, wherein the multifunctional polymer comprises at least two functional groups that can react with specific groups of the carrier base material to form a cross-linked matrix. The demineralized bone carrier matrix may further comprise a ceramic material which may be, but not limited to allograft cortical or cancellous bone chips, hydroxyapatite, tricalcium phosphate, calcium sulfate or combinations thereof. Methods are also provided for making and using the demineralized bone carrier matrix. It is contemplated that the material will be used as a bone graft substitute.

The demineralized bone carrier matrix of the present invention has good flexibility and is compression resistant. It is also is osteoinductive with the demineralized bone matrix retaining activity within the matrix. These properties make the material an excellent bone graft substitute in that it may not break, crack or deform when implanted in the body, particularly the spine. The use of a multifunctional polymer to cross-link the carrier base material without additional chemicals and compounds allows for the trapping of the demineralized bone within a flexible and strong matrix without inactivating the demineralized bone. Most chemical cross-linking agents inactivate demineralized bone matrix, not allowing a strong cross-linked matrix before the present invention.

In one embodiment of the present invention there is provided a demineralized bone carrier matrix comprising a crosslinked matrix having demineralized bone (DBM) dispersed within and optionally throughout the crosslinked matrix. The crosslinked matrix comprises a carrier base material and a multifunctional polymer which cross-links the carrier base material. The functional groups of the multifunctional polymer react under mild conditions with the carrier base material without the addition of other cross-linking agents. The carrier base material may be any material that provides a good base for the matrix and has a sufficient number of reactive groups to cross-link with the multifunctional polymer. Reactive groups may be, but not limited to, amines, amides, thiols, hydroxyls and carboxylates. In one illustrative embodiment, the carrier base material may be a gelatin or purified collagen. The gelatin may be commercially obtained or it may be produced from DBM by autoclaving the DBM in an aqueous saline solution at about 121° C. for about one hour. The DBM may be fully or partially demineralized. The gelatin may be made and then stored to be used as needed.

In an alternate illustrative embodiment, the carrier base material may be another protein based material such as, but not limited to, polylysine, plasma, platelet rich plasma (PRP), platelet poor plasma (PPP), fibrin or fibrinogen. The plasma, PRP or PPP may be concentrated. These materials are known to react with multifunctional polymers having amine/amide reactive functional groups. The use of plasma, PRP or PPP may also provide additional growth factors in addition to the osteoinductive factors found in the DBM.

In yet another illustrative embodiment, the carrier base material may be other polymers such as, but not limited to, carbohydrates, polyamines, polycarboxylic acids, self-assembling hydrogels and synthetic polyamino acids.

In a further embodiment, the carrier base material may comprise from about 10 wt % to about 30 wt % of the demineralized bone carrier matrix based on the dry weight of the demineralized bone carrier matrix.

In another embodiment, the multifunctional polymer has a functionality of at least two. In an illustrative embodiment, the multifunctional polymer has a functionality of from about 2 to about 4. In an additional illustrative embodiment, the multifunctional polymer has a functionality of from about 2 to about 8. The functionality is an expression of the number of functional groups found on the multifunctional polymer available to interact with reactive groups of the carrier base material.

The functional groups may be selected to selectively react with thiols, amines, carboxylic acids or they may be non-specific. Functional groups that react with thiols may be, but not limited to, vinylsulfone, N-ethyl maleimide, iodoacetamide, acrylate, thiol, epoxide and orthopyridyl disulfide. Alternatively, functional groups that specifically react with amines may be, but not limited to, aldehydes, N-hydroxysuccinimide (NHS), isocyanate, epoxide and acrylate. Functional groups that are non-selective may be, but not limited to, active esters, epoxides, azides, carbonylimidazole, nitrophenyl carbonates, tresylate, mesylate, tosylate and isocyanate. In an illustrative embodiment, the functional groups of the multifunctional polymer may be capable of binding to free amino groups of the carrier base material. By way of non-limiting example, gelatin has a significant number of lysine residues. Similarly, proteins such as, but not limited to, collagen, fibrin, fibrinogen or other plasma proteins, may have lysine residues available for reacting with the multifunctional polymer. Therefore it may be desirable to have a multifunctional polymer with functional groups that can bind to the available lysine residues of collagen or other common plasma proteins. In an exemplary embodiment, the functional group may be an ester of N-hydroxysuccinimide such as a succinimidyl glutarate ester or a succinimidyl carboxy methyl ester.

In a further embodiment, the multifunctional polymer may be a hydrophilic biocompatible polymer. Non-limiting examples of hydrophilic biocompatible polymers that may be used in the present invention may be poly(ethylene glycol), poly(ethylene oxide), poly(vinyl alcohol), poly(vinylpyrrolidine), poly(ethyloxazoline), poly(ethylene glycol)-co-poly(propylene glycol) block polymers or combinations thereof. In an exemplary embodiment, the hydrophilic polymer may be poly(ethylene glycol) or poly(ethylene oxide). Additionally, the polymer may be linear or it may be multi-armed (multi-branched). In an illustrative embodiment, a multi-armed polymer may comprise at least three arms. In another illustrative embodiment, a multi-armed polymer may have from about 3 to about 8 arms. In a further illustrative embodiment, the protein binding agent may comprise a 4-arm poly(ethylene glycol) succinimidyl glutarate or a 4-arm poly(ethylene oxide) succinimidyl glutarate.

The multifunctional polymer may be homofunctional or heterfunctional. A homofunctional polymer may have at least two functional groups wherein all functional groups are identical, no matter how many. A heterfunctional polymer may have at least two functional groups wherein there are at least two different functional groups.

The multifunctional polymer may have a molecular weight of from about 1,000 to about 30,000. In an illustrative embodiment, the multifunctional polymer may have a molecular weight of from about 2,000 to about 10,000. In another illustrative embodiment, the multifunctional polymer may have a molecular weight of from about 2,000 to 4,000 or from about 3,000 to 4,000.

The concentration of the multifunctional polymer with respect to the demineralized bone carrier matrix may be dependent on the nature of the multifunctional polymer as well as the carrier base material, including the functionality and the reactivity of the functional groups and/or the concentration of reactive groups in the carrier base material. In one illustrative embodiment, the concentration of multifunctional polymer may be from about 0.1 wt % to about 4.0 wt % or from about 0.2 wt % to about 2.5 wt % based on the dry weight of the demineralized bone carrier matrix. It is well within the ability of the skilled artisan to determine the optimal amount of multifunctional polymer without undue experimentation.

In one illustrative embodiment, the molar ratio of functional groups of the multifunctional polymer to the reactive groups of the carrier base material may be less than 1:11. A higher molar ratio (i.e. 1:35) will give a cross-linked matrix that will either not gel, or will be too flexible and will deform. If the ratio is too high, the carrier matrix may be brittle and too fragile. The molar ratio can be calculated if the number of functional groups and the number (or a good estimate) of the reactive groups of the carrier base material are known. For example, if the multifunctional polymer is a bi-succinimidyl glutarate ester PEG (PEG-$(NHS)_2$) and the carrier base material is DBM-derived gelatin, the molar ratio, or conversely the amount of material required to give a specific ratio can be calculated as follows. The ratio of activated PEG-$(NHS)_2$ to gelatin may calculated based upon the number of activated PEG-NHS end-groups to lysines in the gelatin. This NHS: lysine molar ratio is calculated using the following numbers: Moles of lysine=(dry weight of gelatin)(1 gram collagen/1 gram gelatin)(290,000 moles collagen/gram of collagen)(70 lysine residues/mole of type I collagen) and Moles of NHS end groups=((dry weight of NHS-PEG)/(Mw of NHS-PEG))(# of NHS end groups per mole of NHS-PEG)

In a further embodiment, the demineralized bone carrier matrix comprises demineralized bone dispersed within the carrier matrix. It is desirable, but not necessary to have it dispersed homogenously (or as near to homogenously as possible) throughout the carrier matrix. The DBM may be fully or partially demineralized. Fully demineralized DBM may have a calcium content of from about <1 wt % to about 8 wt % while partially demineralized bone may have a calcium content of from above 8 wt % to an amount below fully mineralized bone. The DBM should have osteoinductive activity and that activity should remain in the demineralized bone carrier matrix. The DBM may be in the form of powder, fine particles or small chips. In an illustrative embodiment, the size of the DBM may be from about 10 μm to about 1500 μm. In one illustrative embodiment, the DBM may comprise from about 0 wt % to about 70 wt % of the demineralized bone carrier matrix. In an alternate illustrative embodiment, the DBM may comprise from about 1 wt % to about 80 wt % of the carrier matrix. In yet another alternate illustrative embodiment, the DBM may comprise from about 0 wt % to about 85 wt % of the carrier matrix or from about 25 wt % to about 90%.

In a further embodiment, the demineralized bone carrier matrix may further comprise a ceramic component such as, but not limited to, allograft cortical or cancellous bone chips. Alternatively, the ceramic component may be ceramic-based bone substitute materials such as, but not limited to, hydroxyapatite, tricalcium phosphate, calcium sulfate or combinations thereof. Non-limiting examples of a ceramic-based bone substitute material would be Pro Osteon© 500R or 200R. The ceramic component may provide additional resistance to compression as well as be an excellent osteoconductive component. In an illustrative embodiment, the ceramic component comprises from about 0 wt % to about 70 wt % of the carrier matrix. In another illustrative embodiment, the ceramic component may comprise from about 20 wt % to about 80 wt % of the carrier matrix or from about 25 wt % to about 90 wt %.

In yet another embodiment, the demineralized bone carrier matrix may comprise other components such as cells, drugs, growth factors or any other therapeutic compound. The cells may be natural cells or they may be genetically engineered to produce a desired therapeutic compound. It will be appreciated that because of the mild conditions (pH 7-9 in most cases) in which cross-linking may occur between the multifunctional polymer and the carrier base material, additional components may easily be added to the carrier matrix.

The present invention also provides methods for making the demineralized bone carrier matrix of the present invention. In one embodiment, the demineralized bone carrier matrix is made by mixing a carrier base material solution with a multifunctional polymer solution to form a carrier matrix precursor. Both the carrier base material solution and multifunctional polymer solutions comprise an aqueous solvent such as, but not limited to, water or a saline solution such as PBS or TBS. The choice aqueous solvent along with the volumes and concentrations of each solution will depend on the composition of the final product as well as the amount of material to be made.

The method also comprises the step of adding demineralized bone matrix to either the carrier base solution or to the carrier matrix precursor. It is not crucial as to when and which solution or mixture the DBM is added to. The DBM may be added as a dry component or it may be partially or fully dehydrated. The advantage to pre-hydrating the DBM is that the adsorption of solvent by the DBM will not need to be considered when determining volumes and concentrations. If a ceramic component is desired it may be added in the same step with the DBM in the same manner. It may also be pre-hydrated, either fully or partially, if desired. After all three components have been added together, the carrier matrix precursor is mixed for a limited period of time to homogenously disperse the DBM. However, stirring should not occur once the carrier matrix precursor begins to gel as air may become trapped in the gel, compromising the structural integrity of the carrier matrix.

The carrier matrix precursor may then be shaped by methods known in the art such as molding. The carrier matrix precursor may be poured into the mold while it can still flow. This time when before it begins to gel is the work time and it is dependent on the concentrations and composition of the materials used. Work time may be defined as the time of which the carrier matrix precursor mixture remains in flowing liquid state, allowing the addition of other ingredients and manipulation. The working time may be influenced by the temperature of the mixture, the concentration of carrier base material, and the multifunctional polymer concentration. The higher the concentrations, the shorter the work time; thus, lowering the carrier base material and/or multifunctional polymer concentrations would imbue the mixture with a longer working time. It will be appreciated that there may be minimal thresholds for the concentrations to achieve the desired product.

Once it is molded the carrier matrix precursor may gel at either ambient temperature or at a lower temperature to form the demineralized bone carrier matrix. The time and temperature will depend on the components used as well as their concentrations. The time and temperature needed can be empirically determined by the skilled artisan without undue experimentation. Gelling times at ambient temperature may range from about 2-5 minutes to overnight.

In an alternate embodiment, the demineralized bone carrier matrix may be shaped instead of the carrier matrix precursor. The carrier matrix precursor may be allowed to gel in a form such as, but not limited to, a block or a sheet. The demineralized bone carrier matrix may then be made into the desired shape by stamping, cutting or other means known in the art.

In another embodiment, the carrier matrix may be lyophilized. In an additional embodiment, the carrier matrix may be sterilized by, but not limited to, gamma irradiation.

EXAMPLE 1

In Vitro Osteoinductivity of DBM in the Carrier Matrix

A 30% w/v gelatin solution was prepared by heating bovine DBM in saline and autoclaved at 121° C. for 1 hour. 0.123 g NHS-PEG-NHS (Creative Biotechnology LLC) was dissolved in 2 ml distilled $H_2O$ at room temperature, then sterilized using a 0.22 μm vacuum filter. After heating the gelatin to 45° C., 3 ml of the gelatin solution was mixed with 2 g human DBM (hDBM) using a glass stir rod. The 2 ml of NHS-PEG solution was then added and the mixture stirred before being allowed to gel at room temperature. Once the mixture gelled, it was cut into halves, and then freeze-dried over a 44-hour cycle. One of the halves was then sterilized with low-dose gamma irradiation (17.2 kGy to 22.6 kGy) while on dry ice. The carrier matrix samples were then tested for osteoinductivity using both an in vitro test with C2C12 cells and in vivo tests of bone formation after implantation in muscle tissue of rats (Han, B et al.,(2003) *J. Orthop. Res.* 21, 648.)(See Example 2). The dry weight composition of the freeze-dried product was 66.2% hDBM, 29.8% gelatin, and 4.1% bifunctional NHS-PEG.

In vitro activity was determined by the amount of alkaline phosphatase activity as compared to a control sample (alkaline phosphatase assay; normalized to 100% DBM content, as percent of unirradiated control DBM). In the in vitro test, there was no affect on the level of osteoinductivity of the DBM by the activated PEG as judged by the cell response when normalized to 100% DBM content as determined by the level of alkaline phosphatase activity. The results are listed in Table 1.

TABLE 1

In vitro osteoinductivity of DBM samples

| | DBM powder | irradiated DBM | PEG-DBM-gelatin | irradiated PEG-DBM | Negative Control[1] |
|---|---|---|---|---|---|
| specimen 1 | 0.912 | 0.613 | 0.64 | 0.533 | 0.163 |
| specimen 2 | 1.138 | 0.692 | 0.674 | 0.583 | 0.144 |
| specimen 3 | 0.958 | 0.665 | 0.799 | 0.462 | 0.138 |
| specimen 4 | 0.942 | 0.618 | 0.528 | 0.434 | 0.177 |
| Average of four | 0.988 | 0.647 | 0.660 | 0.503 | 0.156 |
| standard deviation | 0.102 | 0.038 | 0.112 | 0.068 | 0.018 |
| normalized to 100% DBM | 0.988 | 0.647 | 0.957 | 0.729 | 0.156 |

[1](negative control = guanidine extracted DBM)

EXAMPLE 2

In Vivo DBM Activity in the Carrier Matrix

The test articles identified below were evaluated for the effectiveness of the test materials to induce bone formation when implanted in heterotopic sites in an athymic rat model. The results from the test articles were compared to the results from the control materials.

The samples were DBM (Test article 1), gamma-irradiated DBM (Test article 2), demineralized bone carrier matrix (Test article 3) and gamma-irradiated demineralized bone carrier matrix (Test article 4). The test articles were cut into 6 mm×6 mm squares in a sterile hood before implantation. The test articles were implanted into Harlan male rats (Hsd: Rh-rnu homozygous), 5-6 weeks old and weighed 150 to 179 grams at the time of implantation. There were 12 animals in all and four samples per test group. The test articles were implanted (IM) for 28 days before being removed. The levels of alkaline phosphatase and histology were used for determining the osteoinductivity for each sample. All animals appeared clinically normal throughout the duration of the study.

As seen in the results in Tables 2 and 3, the histology and alkaline phosphatase activity assays are in agreement. The results are also consistent with the results of the in vitro analysis. Both of the demineralized bone carrier matrix samples had less activity than the DBM control sample, but significantly more than the gamma-irradiated DBM sample.

TABLE 2

Alkaline Phosphatase (AP) activity in explants:

| Test Article | Sample ID | AP/Pro | StDev[1] |
|---|---|---|---|
| T1 | DBM Pos | 2.484 | 0.618 |
| T2 | DBM pos Gamma | 1.073 | 0.503 |
| T3 | Gelatin-DBM-PEG | 1.472 | 0.1118 |
| T4 | Gelatin-DBM-PEG Gamma | 1.134 | 0.126 |

[1]n = 6

TABLE 3

Microscopic evaluation

| Sample name | | | | | | | Bone score[1] Ave | StDev |
|---|---|---|---|---|---|---|---|---|
| T1 DBM | 2 | 3 | 2 | 1 | 3 | 3 | 2.33 | 0.82 |
| T2 DBM gamma | 1 | 1 | 2 | 1 | 2 | 2 | 1.50 | 0.55 |
| T3 Gel-DBM-PEG | 1 | 0 | 2 | 3 | 2 | 2 | 1.67 | 1.03 |
| T4 Gel-DBM-PEG Gamma | 1 | 1 | 2 | 1 | 2 | 0 | 1.17 | 0.75 |

[1]Microscopic Scoring Scheme:
0 = 0% of implant area occupied by new bone/cartilage
1 = 1-20% of implant area occupied by new bone/cartilage
2 = 20-45% of implant area occupied by new bone/cartilage
3 = 45-70% of implant area occupied by new bone/cartilage
4 = >70% of implant area occupied by new bone/cartilage

EXAMPLE 3

Bifunctional PEG v. Multifunctional PEG in the Carrier Matrix

Demineralized bone carrier matrix formulations were created with both 2-arm NHS-PEG (bifunctional) and 4-arm NHS-PEG (multifunctional). The specific compounds used had end-terminal groups of succinimidyl glutarate. The 2-arm NHS-PEG-NHS had a molecular weight of about 3.4 kDa (Creative Biotechnology LLC), and the 4-arm PEG-NHS had a molecular weight of about 10 kDa (Sigma). The formulations shown in Table 4 were successful in creating crosslinked matrices as tested by physical stability after one hour in 47° C. water.

TABLE 4

| Gelatin | NHS-PEG | DBM | Crosslinked |
|---|---|---|---|
| 3 ml 30% gelatin | 0.123 g 2-arm NHS-PEG in 0.1 ml water | 1 gram dry powder | Yes |
| 3 ml 30% gelatin | 0.123 g 2-arm NHS-PEG in 0.1 ml water | 1.5 gram dry powder | Yes |
| 3 ml 30% gelatin | 0.123 g 2-arm NHS-PEG in 0.1 ml water | 2.0 gram dry powder | Yes |
| 3 ml 30% gelatin | 0.18 g 4-arm NHS-PEG in 0.1 ml water | 2.0 gram dry powder | Yes |

EXAMPLE 4

Establishment of NHS:Lysine Molar Ratio

The amount of NHS-PEG added to gelatin was varied to establish the minimal amount of NHS-PEG needed to create a crosslinked matrix. The NHS-PEG used in this study was 2-arm succinimidyl-gluarate homobifunctional PEG with a MW of about 3.4 kDa. The gelatin was made from DBM by mixing DBM into a saline solution and autoclaving at 121° C. for 1 hour on the wet cycle to produce a gelatin solution of desired concentration (w/v). For example, to prepare 100 ml of a 20% w/v stock gelatin, 20 g DBM was mixed with 100 ml of an aqueous saline solution and autoclaved as described. Concentration of the stock gelatin solution was varied from 20% to 30% w/v. PEG-(NHS)$_2$ (0.034 g) was weighed in a vessel and 3 ml of distilled water was added to the vessel. The PEG-(NHS)$_2$ was dissolved by agitating and vortexing the mixture.

The stock gelatin solution was heated on a hot plate to approximately 35° C. to 40° C. to maintain gelatin in a liquid state and workable condition. Note that the temperature may vary with stock concentration, but usually 35° C. or above may be necessary. If active bone chips or DBM are to be incorporated into the crosslinked gelatin, the temperature needs to be kept below 60° C. to prevent denaturation of growth factors in the bone chips or DBM.

Work time is defined as the time of which the gelatin/PEG-(NHS)$_2$ mixture remain in flowing liquid state, allowing addition of other ingredients and manipulation. The working time of gelatin/PEG-(NHS)$_2$ mixture is influenced by the temperature of mixture, the concentration of stock gelatin, and the PEG-(NHS)$_2$ concentration. The higher the PEG-(NHS)$_2$ and gelatin concentrations, the shorter the work time; thus, lowering PEG-(NHS)$_2$ and gelatin concentrations would imbue the mixture longer working time. Note there are minimal thresholds for PEG-(NHS)$_2$ and gelatin concentrations to achieve successfully crosslink gelatin; refer to Results section for further details. Keeping the crosslinking mixture at elevated temperature will extend its work time, but only to certain extent, which needed to be determined empirically.

To crosslink the gelatin, 3 ml of stock gelatin was transferred to another vessel on a hot plate and 3 ml of the PEG-(NHS)$_2$ solution was added to the gelatin solution. The mixture was stirred by hand for about 1 minute to ensure homogenous mixing of the components and then removed from the hot plate.

The pH of gelatin as prepared above using saline and DBM (30% w/v) was determined to be roughly 6.8 using a pH meter which falls in the range (7-9) suitable for the PEG-NHS crosslinking reaction. Measurements of pH using pH test paper yielded similar results, indicating that stock gelatin has near-neutral pH, consistent with measurements using pH probe.

Crosslinking was determined by observing whether the matrix dissolved after an hour in 47° C. water. Molar ratios of 1:11.67 NHS:Lysine or higher (i.e. 1:35) did not result in a crosslinked matrix as shown in Table 5.

TABLE 5

| Stock Gelatin Conc. (% w/v) | Final Gelatin Conc. (% w/v) | NHS:Lysine Molar Ratio | Crosslink |
| --- | --- | --- | --- |
| 20 | 10 | 1:35 | NO |
| 20 | 10 | 1:11.67 | NO |
| 20 | 10 | 1:7 | Yes |

TABLE 5-continued

| Stock Gelatin Conc. (% w/v) | Final Gelatin Conc. (% w/v) | NHS:Lysine Molar Ratio | Crosslink |
| --- | --- | --- | --- |
| 20 | 10 | 1:5 | Yes |
| 20 | 10 | 1:3.5 | Yes |
| 25 | 12.5 | 1:35 | NO |
| 25 | 12.5 | 1:11.67 | NO |
| 25 | 12.5 | 1:7 | Yes |
| 25 | 12.5 | 1:5 | Yes |
| 25 | 12.5 | 1:3.5 | Yes |
| 30 | 15 | 1:35 | NO |
| 30 | 15 | 1:11.67 | NO |
| 30 | 15 | 1:7 | Yes |
| 30 | 15 | 1:5 | Yes |
| 30 | 15 | 1:3.5 | Yes |

EXAMPLE 5

Effect of Final Gelatin Concentration

Bovine gelatin made by autoclaving bovine demineralized bone (particle size less than 710 microns) for 60 minutes in saline. The following starting concentrations were made: 10%, 15%, 20%, 25%, 30%.

Three ml of gelatin was mixed with three ml of PEG-NHS dissolved in water. The amount of PEG-NHS was calculated to keep a molar ratio of 1 NHS reactive group on the NHS PEG to 3 lysine residues in the gelatin. The activated PEG was a 3400 MW bifunctionalized PEG with succinyl reactive groups (two NHS groups) from Creative Biochemical LLC.

The gelatin-PEG mixtures were allowed to set at room temperature overnight, after which they were placed in 50 cc tubes with 30 ml water and placed in 48° C. bath for one hour. If intact after one hour, they were considered crosslinked. As shown in Table 6, the 20%, 25%, and 30% gelatins crosslinked while the 10% and 15% did not.

TABLE 6

| percent gelatin (3 mls) | amount of PEG in 3 mls water | final gelatin concentration | crosslink |
| --- | --- | --- | --- |
| 10 | 0.040 g | 5 | no |
| 15 | 0.059 | 7.5 | no |
| 20 | 0.081 | 10 | yes |
| 25 | 0.100 | 12.5 | yes |
| 30 | 0.120 | 15 | yes |

EXAMPLE 6

Pre-Hydration of DBM and Pro Pro Osteon©

Previous experimentation where the DBM was added to the gelatin/PEG-(NHS)$_2$ mixture resulted in problems caused by water absorption by the DBM. Pro Pro Osteon© granules also absorb water due to its porosity so the water up take by both DBM and Pro Pro Osteon© in a sample may reduce water content of the gelatin/PEG-(NHS)$_2$ mixture, leading to increased viscosity and shortened work time. In addition, agitation of such a viscous mixture introduced many air bubbles of different sizes, compromising the integrity of the carrier matrix. These issues are undesired in terms of processing.

Pre-hydration of DBM and Pro Pro Osteon© prior to the addition of gelatin and PEG-(NHS)$_2$ solutions may avoid water absorption from the gelatin/PEG-(NHS)$_2$ mixture during crosslinking. An experiment was conducted to evaluate the amount of water necessary to hydrate DBM and Pro Osteon©. DBM or Pro Osteon© 200R (1 g) were loaded in 15 ml centrifuge tubes; different volumes of water were added and then the hydration of DBM and Pro Osteon© was observed visually over time. The tubes were capped during the hydration time to prevent water evaporation, and hydration was conducted statically without agitation.

The results of the pre-hydration of DBM and Pro Osteon© are shown in Table 6. Full hydration is defined as when all the DBM or Pro Osteon© loaded in the tubes becomes wet after addition of water. The observations were made immediately after water addition, and again on the following day after samples were left on a bench top overnight. If the material's hydration state did not change between the two observations, its hydration is final and graded to have a fast hydration rate. However, if the material continued to hydrate after the first observation, it is graded as having a slow hydration rate. Excess fluid is defined as a layer of water seen on top of material, indicating excessive water addition.

The results indicate that 2.5 ml to 3 ml of water is enough to fully hydrate 1 g of DBM, and volumes larger than 3 ml are excessive. It was also observed that 0.5 ml water is sufficient to hydrate 1 g of Pro Osteon©. Moreover, the experiment revealed significant differences in the water absorption rates between DBM and Pro Osteon© in a static condition (no mixing) with Pro Osteon© taking up water rapidly while DBM absorbed water slowly over a few hours.

TABLE 6

DBM & ProOsteon 200R Hydration

| Sample # | DBM Weight (g) | Pro Osteon © 200R Weight (g) | Water Addition Volume (ml) | Full Hydration | Excess Fluid | Hydration Rate |
|---|---|---|---|---|---|---|
| 1 | 1 | 0 | 1.0 | No | No | Slow |
| 2 | 1 | 0 | 1.5 | No | No | Slow |
| 3 | 1 | 0 | 2.0 | No | No | Slow |
| 4 | 1 | 0 | 2.5 | Yes | No | Slow |
| 5 | 1 | 0 | 3.0 | Yes | Yes | Slow |
| 6 | 1 | 0 | 3.5 | Yes | Yes | Slow |
| 7 | 0 | 1 | 0.5 | Yes | No | Fast |
| 8 | 0 | 1 | 0.625 | Yes | No | Fast |
| 9 | 0 | 1 | 0.75 | Yes | No | Fast |
| 10 | 0 | 1 | 1.0 | Yes | Yes | Fast |

EXAMPLE 7

Carrier Matrix with Both DBM and Pro Osteon©

The demineralized bone matrix samples of different formulations were prepared following the process detailed here, unless otherwise specified. Samples of DBM and Pro Osteon© granules were weighed and then mixed within a vessel. Mixing was applied until uniform distribution of DBM and Pro Osteon© was achieved. A set volume of water was added to the mixture to pre-wet the DBM and Pro Osteon©. Active stirring was applied to ensure uniform water absorption. The mixture was stirred for several minutes (about 2 minutes to about 10 minutes) to allow DBM to hydrate due to its slower hydration rate as compared to Pro Osteon© (see Table 6).

The gelatin solution was heated on a hot plate to a temperature that was sufficient to maintain it in a liquid state and workable condition. The temperature should be low enough to prevent denaturation of osteoinductive proteins in DBM and to reduce water evaporation from the gelatin solution. 3 ml of gelatin solution was added to 3 ml of a PEG-(NHS)$_2$ solution in a different vessel. The mixture was stirred by hand for 15 to 30 seconds to ensure good mixing.

After DBM and Pro Osteon© were pre-hydrated, the 6 ml of gelatin/PEG-(NHS)$_2$ solution was added to the DBM and Pro Osteon© mixture. The mixture was stirred by hand for less than 30 seconds to ensure homogeneous mixing, and then allowed to gel statically on a bench top at ambient conditions.

Once the carrier matrix had gelled, it was retrieved from the vessel and evaluated for handling and crosslinking. To test for crosslinking, a piece of the carrier matrix sample was placed in a 50 ml centrifuge tube with roughly 30 ml of water. The sample was then immersed in 48° C. water bath for at least 10 minutes. If the carrier matrix sample dissolved and disintegrated, it was marked as not crosslinked but if the sample remained intact, it was marked as crosslinked. For handling evaluation, samples underwent compression, bending, and stretching, being observed visually.

Sixteen different carrier matrix samples were formulated and evaluated are shown in Table 7. The amount of PEG-(NHS)$_2$ added was kept constant as well as gelatin content, which was at 0.6 g dry weight. Thus, the PEG-(NHS)$_2$ to gelatin molar ratio remained 5 to 1 for all formulations.

Samples 1 to 5 contained either DBM or Pro Osteon© to evaluate the addition of wet Pro Osteon© or DBM in PEG-(NHS)$_2$ crosslinked gelatin separately.

Samples 6, 7, and 8 show the results of hydrating the DBM and Pro Osteon© using the water content of the gelatin solution without pre-hydration, hence a larger volume but lower concentration to keep the gelatin content in the reaction constant. In sample 6, DBM and Pro Osteon© granules were mixed uniformly, then the gelatin solution was added to hydrate the mixture. The PEG-(NHS)$_2$ solution was added last. Samples 7 and 8 followed the standard process as given above, using both water addition and larger gelatin volumes to hydrate DBM and Pro Osteon©.

Samples 9 and 10 show the effect of pre-hydration of the DBM and Pro Osteon© mixture with water prior to crosslinking. Samples 9 and 10 have the same ingredient compositions, but sample 9 was prepared with the gelatin and PEG-(NHS)$_2$ solutions being mixed before addition to the pre-hydrated DBM and Pro Osteon© mixture. In contrast, sample 10 was prepared by adding the gelatin to the pre-hydrated DBM and Pro Osteon© mixture before the PEG-(NHS)$_2$ solution was added to the gelatin/DBM/Pro Osteon© mixture.

Samples 11 to 16 show the effect of partially hydrating the DBM and Pro Osteon© mixture with water in contrast to fully hydrating the sample in order to reduce the volume of water added. Sample 14 is the same as sample 12 in both the process and ingredient composition. Sample 12 sample was prepared using a PEG-(NHS)$_2$ solution prepared a day prior to experiment, while sample 14 was prepared using a freshly made PEG-(NHS)$_2$ solution.

TABLE 7

PEG-(NHS)$_2$ Crosslinked demineralized bone matrix formulations

| Sample | DBM (g) | Pro Osteon © (g) | Gelatin (ml) | Gelatin (% w/v) | PEG Sol'n (ml) | PEG:Gel Molar Ratio | Water (ml) |
|---|---|---|---|---|---|---|---|
| 1 | 1 | 0 | 3 | 20 | 3 | 5:1 | 3 |
| 2 | 1 | 3 | 3 | 20 | 3 | 5:1 | 3.5 |
| 3 | 1 | 3 | 3 | 20 | 3 | 5:1 | 4 |
| 4 | 0 | 2 | 3 | 20 | 3 | 5:1 | 1 |
| 5 | 0 | 2 | 3 | 20 | 3 | 5:1 | 1.5 |

TABLE 7-continued

PEG-(NHS)₂ Crosslinked demineralized bone matrix formulations

| Sample | DBM (g) | Pro Osteon© (g) | Gelatin (ml) | Gelatin (% w/v) | PEG Sol'n (ml) | PEG:Gel Molar Ratio | Water (ml) |
|---|---|---|---|---|---|---|---|
| 6 | 3 | 2 | 12 | 5 | 3 | 5:1 | 0 |
| 7 | 3 | 2 | 6 | 10 | 3 | 5:1 | 8 |
| 8 | 3 | 2 | 6 | 10 | 3 | 5:1 | 3 |
| 9 | 3 | 2 | 3 | 20 | 3 | 5:1 | 8 |
| 10 | 3 | 2 | 3 | 20 | 3 | 5:1 | 8 |
| 11 | 1.5 | 1.0 | 3 | 20 | 3 | 5:1 | 4 |
| 12 | 1 | 1 | 3 | 20 | 3 | 5:1 | 4 |
| 13 | 1 | 0.5 | 3 | 20 | 3 | 5:1 | 3 |
| 14 | 1 | 1 | 3 | 20 | 3 | 5:1 | 4 |
| 15 | 1.5 | 0.5 | 3 | 20 | 3 | 5:1 | 3 |
| 16 | 1.5 | 1 | 3 | 20 | 3 | 5:1 | 3 |

The results of the carrier matrix sample evaluation are summarized in Table 8.

TABLE 8

PEG-(NHS)₂ Crosslinked CRM Formulation Evaluations

| Formulation # | Crosslinking | Comments |
|---|---|---|
| 1 | Yes | Handled similar to crosslinked gelatin without DBM; surface was smooth; appeared firm and is tolerant to bending, stretching, and compression; DBM mostly embedded at bottom due to gravity |
| 2 | Yes | No observable difference from Formulation 1 |
| 3 | Yes | No observable difference from Formulation 1 |
| 4 | Yes | Handling and appearance close to Formulation 1; Pro Osteon © embedded on bottom due to gravity and making the bottom side susceptible to cracking when bent |
| 5 | Yes | No observable difference from Formulation 4 |
| 6 | No | Did not gel at room temperature |
| 7 | N/a | Did not gel at room temperature; not tested for crosslinking |
| 8 | N/a | Did not gel at room temperature; not tested for crosslinking |
| 9 | Yes | Handled soft and easy to deform under compression; not tolerant of bending or stretching; surface was rough and DBM particulates seemed exposed; crosslinking testing shown heterogeneous crosslinking, with portions of sample disintegrated and the rest remained intact |
| 10 | Yes | Evaluation similar to that of Formulation 9; no observable difference shown |
| 11 | No | Handled fragile and deformed easily under compression; not tolerant to bending or stretching; surface is smooth |
| 12 | No | Handled soft and deform easily under compression, intolerant to stretching and compression, and bending in particular, which led to cracking/breaking |
| 13 | Yes | Handled firm; tolerant to compression, bending, and stretching; surface was mostly smooth but rougher than Formulation 1; Pro Osteon ©/DBM embedded at bottom due to gravity |
| 14 | Yes | Handled firm; tolerant to compression, bending, and stretching; surface texture is similar to Formulation 13 |
| 15 | Yes | Handled firm; tolerant to compression, bending, and stretching; slightly stiffer than Formulation 13 & 14; surface slightly rougher than Formulation 13 & 14 with more air bubbles introduced; Pro Osteon © embedded on bottom due to gravity, but DBM appeared more uniformly distributed than Formulation 13 & 14 |
| 16 | No | Handled firm and tolerant to bending and compression; less flexible than Formulation 13 & 15; surface appearance similar to Formulation 15; DBM and Pro Osteon © slightly more uniformly distributed than Formulation 15 |

First, the carrier matrix must be able to maintain its integrity at physiological temperature. The carrier matrix should also retain the handling characteristics of a PEG-(NHS)₂ crosslinked gelatin, which is tolerant of bending, stretching, and compression. It should be composed of sufficient DBM and, optionally, Pro Osteon© for osteoinductive functions, but also sufficient crosslinked gelatin to hold the individual components and maintain structural cohesion. Desired geometry of the sample may be a rectangular piece with thickness in the range of 0.4 cm to 0.6 cm. The presence of air pockets or bubbles should be reduced as much as possible, and surface should be smooth. Ideally, the process for making the carrier matrix should consist of as few steps as possible to facilitate operation while providing desired degree of control over the process and final product. Lower gelatin concentration may be desired as it may be easier to work with.

Evaluations of samples 1 to 5 showed that the gelatin can be successfully crosslinked with the addition of pre-hydrated DBM and Pro Osteon© under the conditions specified in Table 7. These results also suggest that pre-hydration of DBM and/or Pro Osteon© does not influence the final handling property of crosslinked carrier matrix.

Samples 6, 7, and 8 showed the effect of hydration of DBM and Pro Osteon© by the gelatin solution. Sample 6 utilized only the water in the gelatin solution in attempt to simplify the process and to allow the use of a gelatin solution with lower concentrations. Samples 7 and 8 had combined sources of water for hydration of the DBM and/or Pro Osteon© from both water addition prior to crosslinking (pre-hydration) and from the gelatin solution. This allowed the use of 10 % w/v gelatin instead of 20 % w/v as in the other samples. However, despite the fact that the gelatin content was maintained at 0.6 g per sample, the final mixtures were watery and did not gel at ambient conditions. Sample 6 did not crosslink along with samples 7 and 8. However, hydration of DBM/ Pro Osteon© using solely gelatin solution or a combination of water and gelatin may be acceptable and maybe advantageous without dilution of the original gelatin solution.

Samples 9 and 10 displayed no observable differences between them, suggesting that the change in process sequence did not affect the carrier matrix handling properties. Both samples incorporated large amounts of DBM and Pro Osteon©, and consequently more water was used to pre-hydrate them. The volumes of gelatin and PEG-(NHS)₂ however, did not appear to be sufficient to achieve the desired properties in handling and crosslinking of the carrier matrix. During the crosslinking evaluation, DBM and/or Pro Osteon© were breaking away from regions of the carrier matrix samples, suggesting heterogeneous crosslinking or a lack of scaffold material to maintain structural cohesion. Handling properties of the samples were also poor, lacking bending and compression tolerance. Consequently, DBM and Pro Osteon© were reduced in later samples to achieve better overall handling and structural cohesion.

Samples 11 to 16 were similar in composition with minor differences in DBM, Pro Osteon© and water content. With quantities of DBM and/or Pro Osteon© reduced, it was thought that these formulations would be crosslinked, which was not the case with every sample. Samples 11, 12 and 16 did not crosslink. A comparison between formulation 12 and 14 demonstrated that PEG-(NHS)$_2$ viability is time sensitive once it is dissolved in water, as freshly prepared PEG-(NHS)$_2$ solution produced crosslinked carrier matrix while a solution left on the bench overnight did not. This may have influenced the crosslinking tests of other carrier matrix formulations. Thus, in order to ensure the viability of PEG-(NHS)$_2$ in the crosslinking reaction, it may be necessary to prepare the PEG-(NHS)$_2$ solution immediately before use.

Nonetheless, there weren't significant differences in the appearance and handling of the samples that were crosslinked. Moreover, judging by previous experiences with freeze-dried carrier matrix samples, it is expected that once the carrier matrix samples undergo freeze-drying, the handling properties and the appearance may be altered, which would further reduce the differences between different samples.

Another property noted during the evaluation was the uniformity of component distribution in carrier matrix. Due to gravity, DBM and Pro Osteon© tended to settle over time in the mold before the mixture gelled, producing varying degrees of component separation, often appearing as layers in the samples. It is not certain whether this phenomenon would impact the carrier matrix functionality negatively or not. However, component separation improved with increasing quantities of DBM and Pro Osteon© per gelatin/PEG-(NHS)$_2$ volume since DBM and Pro Osteon© would take up more space inside the carrier matrix and thereby be more tightly packed.

With regard to working time, 20 % w/v gelatin/ PEG-(NHS)$_2$ (1 to 1 volume mixture) with 5 to 1 PEG-(NHS)$_2$ to gelatin molar ratio had a working time longer than 5 minutes in general, and that may be extended if kept warm. If the DBM and/or Pro Osteon© are partially hydrated, as in formulations 11 to 16, the mixture would gel within 5 minutes at room temperature once the gelatin/PEG-(NHS)$_2$ was added to the DBM and/or Pro Osteon©. If the DBM and/or Pro Osteon© were saturated with water prior to gelatin addition, the working time may possibly be lengthened due to dilution of the gelatin concentration. However, this will also likely influence the crosslinking process of carrier matrix due to dilution of the gelatin and PEG-(NHS)$_2$ concentrations, and it may become more difficult to control the volume of water addition because of the excessive water not taken up by DBM and/or Pro Osteon©.

It should be understood, of course, that the foregoing relates to exemplary embodiments of the invention and that modifications may be made without departing from the spirit and scope of the invention as set forth in the following claims.

We claim:

1. A compression resistant osteoinductive demineralized bone carrier matrix comprising:
   a crosslinked matrix, the crosslinked matrix comprising a carrier base material crosslinked with a multifunctional poly(ethylene glycol), wherein the carrier base material is a gelatin and wherein the multifunctional poly(ethylene glycol) has a functionality of about 2 to about 4;
   a demineralized bone matrix, wherein the demineralized bone matrix is dispersed throughout the crosslinked matrix, and wherein the osteoinductive demineralized bone carrier matrix comprises from at least 10 wt% to about 30 wt% of the carrier base material, from about 0.1% to about 4 wt% of the multifunctional poly(ethylene glycol) and from greater than about 55 wt% to about 75 wt% of the demineralized bone matrix with respect to a dry weight of the osteoinductive demineralized bone carrier matrix, and
   a ceramic material consisting of hydroxyapatite and calcium carbonate,
   wherein the demineralized bone carrier matrix, once introduced to an intramuscular implantation site, induces bone formation such that at least 1% of the implantation site is involved in new bone or cartilage.

2. The osteoinductive demineralized bone carrier matrix of claim 1 wherein the multifunctional poly(ethylene glycol) has at least two functional groups.

3. The osteoinductive demineralized bone carrier matrix of claim 1 wherein the multifunctional poly(ethylene glycol) is homofunctional.

4. The osteoinductive demineralized bone carrier matrix of claim 1 wherein the multifunctional poly(ethylene glycol) is heterfunctional.

5. The osteoinductive demineralized bone carrier matrix of claim 1 wherein at least one functional group of the multifunctional poly(ethylene glycol) reacts with an amino group of the gelatin.

6. The osteoinductive demineralized bone carrier matrix of claim 1 wherein at least one of the functional groups of the multifunctional poly(ethylene glycol) is a succinimidyl glutarate ester.

7. The osteoinductive demineralized bone carrier matrix of claim 1 wherein the crosslinked matrix does not dissolve after being exposed for one hour in water having a temperature of 47° C.

8. The osteoinductive demineralized bone carrier matrix of claim 1 wherein the multifunctional poly(ethylene glycol) has a molecular weight of at least 3,000 and no more than 10,000.

* * * * *